(12) United States Patent
Valtchev

(10) Patent No.: US 8,347,888 B2
(45) Date of Patent: Jan. 8, 2013

(54) VAGINAL SPRING LOADED DELINEATOR

(76) Inventor: Konstantin Lazarov Valtchev, Toronto (CA)

( * ) Notice: Subject to any disclaimer, the term of this patent is extended or adjusted under 35 U.S.C. 154(b) by 0 days.

(21) Appl. No.: 12/080,848

(22) Filed: Apr. 8, 2008

(65) Prior Publication Data

US 2008/0249535 A1 Oct. 9, 2008

Related U.S. Application Data

(63) Continuation-in-part of application No. 10/715,104, filed on Nov. 17, 2003, now abandoned.

(51) Int. Cl.
*A61F 6/14* (2006.01)
*A61F 6/06* (2006.01)
*A61B 17/42* (2006.01)
(52) U.S. Cl. .................. 128/839; 128/840; 606/119
(58) Field of Classification Search .......... 128/831, 128/834, 840, 841, 830, 839; 606/119
See application file for complete search history.

(56) References Cited

U.S. PATENT DOCUMENTS

| | | | |
|---|---|---|---|
| 2,818,856 A * | 1/1958 | Kohl | 128/838 |
| 3,952,737 A | 4/1976 | Lipfert | |
| 4,821,741 A | 4/1989 | Mohajer | |
| 5,562,679 A | 10/1996 | Valtchev | |
| 6,423,075 B1 | 7/2002 | Singh et al. | |

* cited by examiner

*Primary Examiner* — Loan Thanh
*Assistant Examiner* — Tarla Patel
(74) *Attorney, Agent, or Firm* — Sturm & Fix LLP

(57) ABSTRACT

A gynaecological instrument for delineating the fornix of the vagina during laparoscopic surgeries having a spring, which proximal end is securely affixed to a distal end of a solid ring and the distal end of the spring is securely affixed to a base. The extension of the base can be inserted into the head of the Valtchev® Uterine Mobilizer and locked in place. When the delineator is pushed toward the fornix of the vagina the solid ring is self-adjusting to the angle of the of the fornix and the length of the cervix. An elastic plastic ring is provided, for placing on the solid ring, in order to protect the ring and instrument which is used to open the vagina laparoscopically.

4 Claims, 8 Drawing Sheets

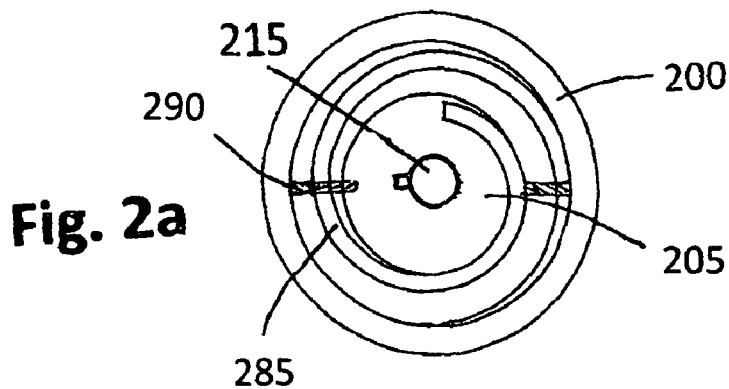
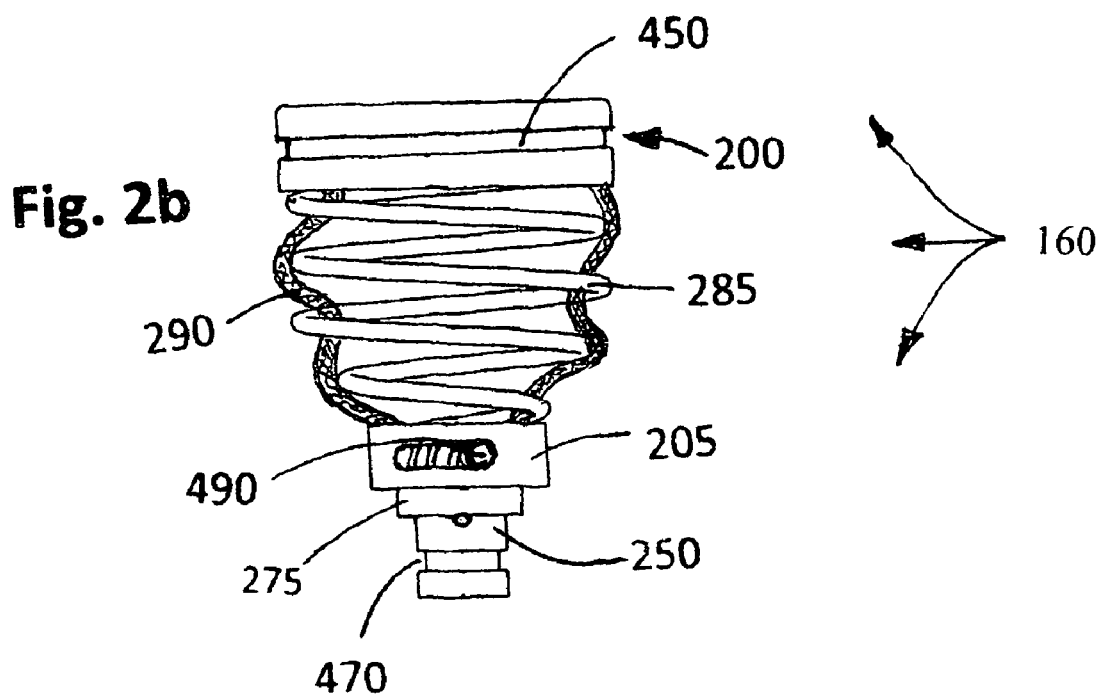
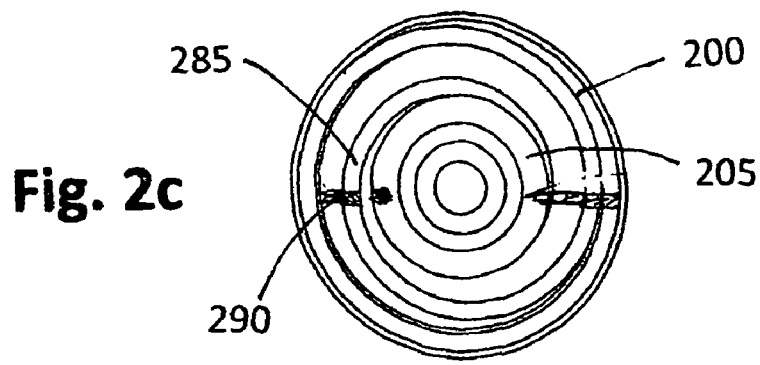

Fig. 3a
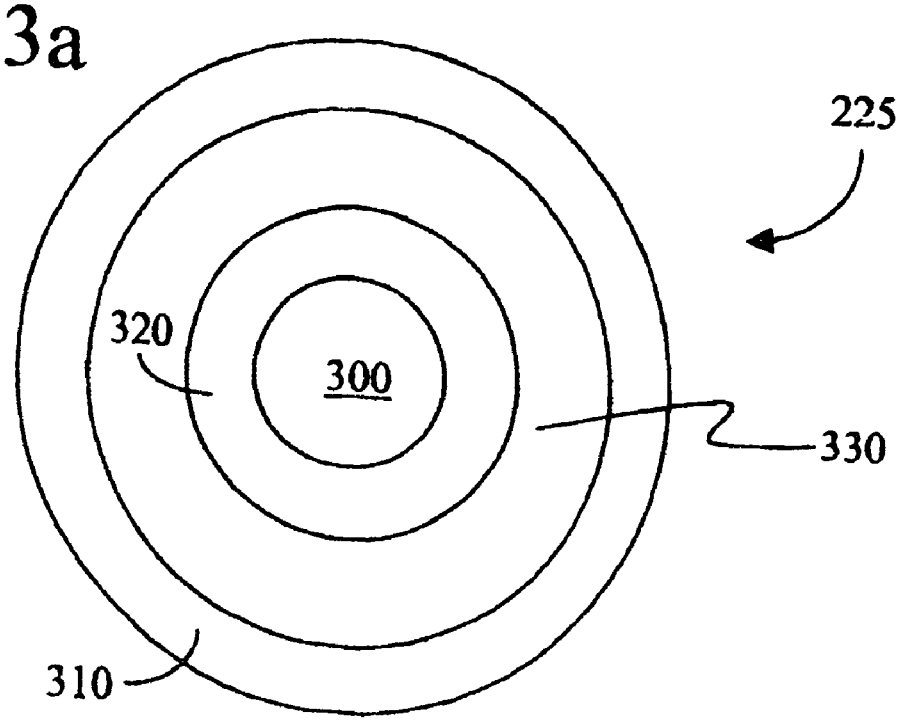
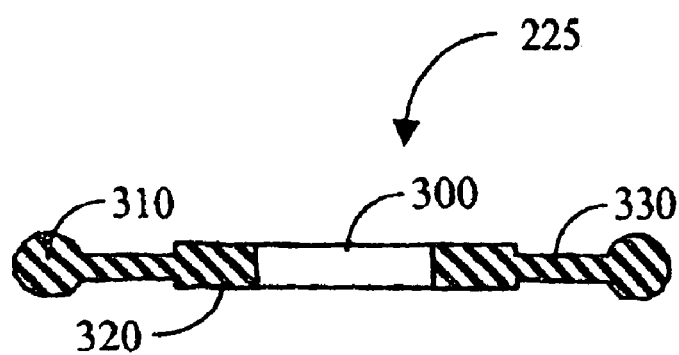
Fig. 3b

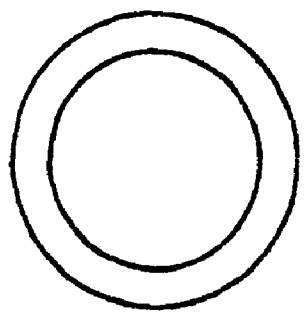
Fig. 5a
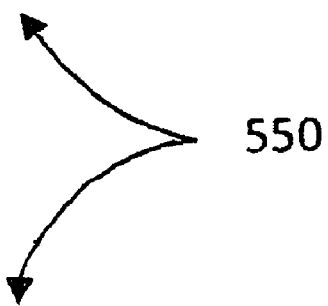
550
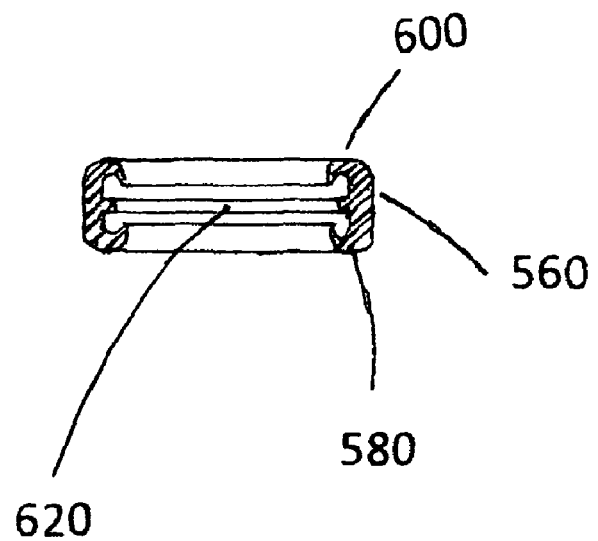
Fig. 5b
600
560
580
620

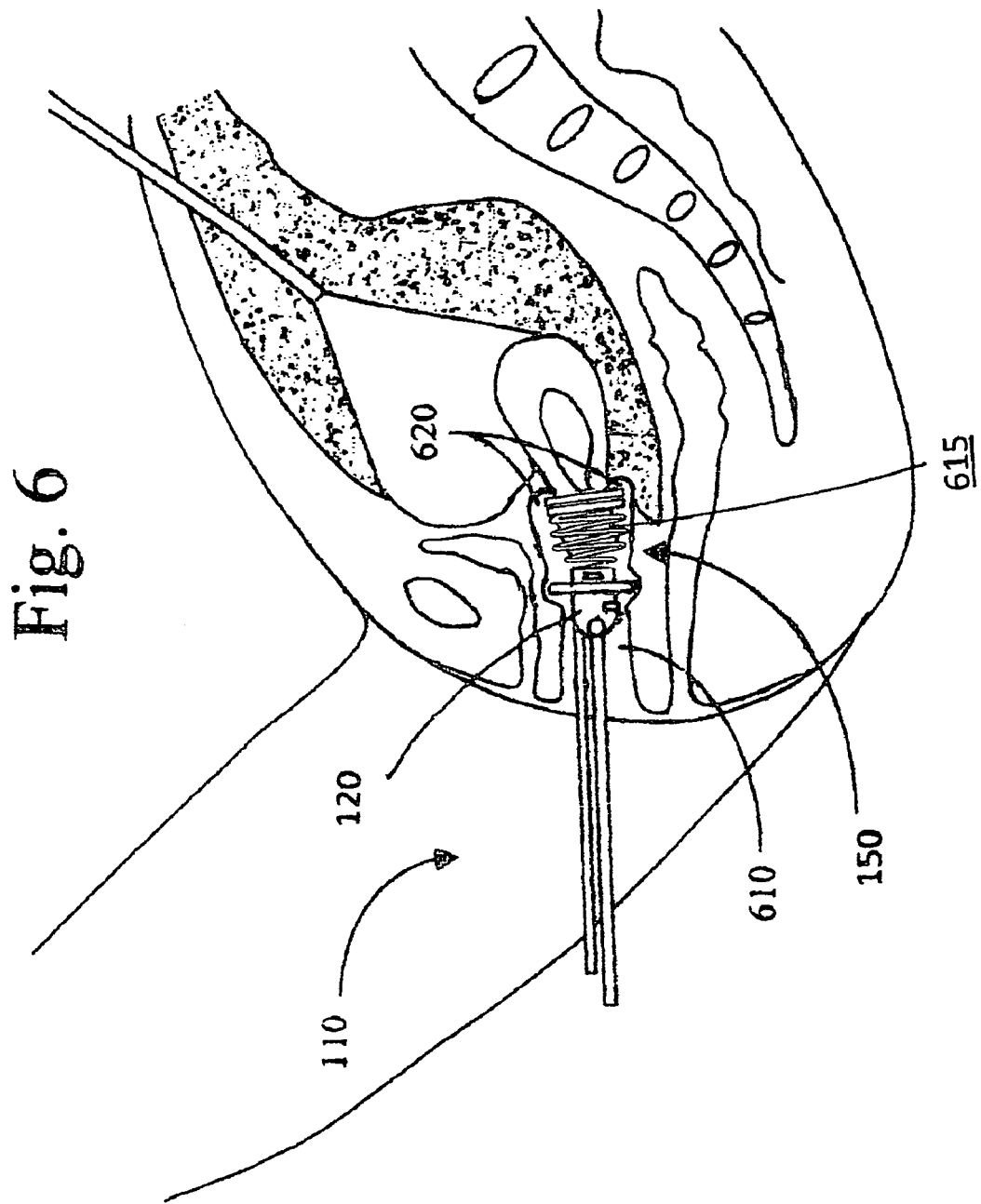

VAGINAL SPRING LOADED DELINEATOR

BACKGROUND OF THE INVENTION

1. Field of the Invention

The present invention relates generally to a gynaecological device. More particularly the present invention relates to a vaginal occlusion and self-adjusting delineation attachment for use with the uterine mobilizer.

2. Background Art

Conventional hysterectomy surgical procedure typically involves one of four approaches: vaginal hysterectomy, total abdominal hysterectomy (TAH), total laparoscopic hysterectomy (TLH), and laparoscopically assisted vaginal hysterectomy (LAVH). Vaginal, TLH and LAVH have become more popular among surgeons because these approaches are less invasive than TAH, with TLH being the least invasive approach. TLH and LAVH are usually viewed as more preferable because each is less invasive when compared to major abdominal surgery. Thus, TLH and LAVH approaches usually result in shorter hospitalization and recovery times. Difficulties arise in TLH and LAVH, however, in identification of the fornix of the vagina if the last is not well delineated. Another technicality is leakage of carbon dioxide from the peritoneal cavity when the vagina is opened laparoscopically.

Another problem, not appropriately addressed in the prior art, is that human bodies vary considerably. Any vaginal insertion device for surgical procedures must, therefore, be adjustable. Such devices are, preferably, self-adjusting.

There is therefore a need for a vaginal delineation device, attachable to a uterine mobilizer that also provides occlusion to the vagina to disallow leakage of carbon dioxide. There is a further need for a vaginal delineation and occluding device that is adjustable, and as self-adjusting as possible

BRIEF SUMMARY OF THE INVENTION

An objective of the present invention is to provide a vaginal delineator for use in gynaecological laparoscopic surgical procedures, which is attached to a uterine mobilizer, such as the Valtchev® Uterine Mobilizer, and is self adjusting to various lengths of cervixes and angles of fornix of the vagina.

The present invention is a device that inserts and locks into a uterine mobilizer, the device comprises a solid ring that adjusts in angle. The ring is made to bear against the vaginal fornix, conforming to its angle and providing delineation of that part of the vagina for identification thereof.

The solid ring is also self-adjusting as to distance from the uterine mobilizer, to accommodate varying lengths of the cervix. This is effected by securely affixing a solid ring to a spring, which has a similar diameter to the diameter of the solid ring. The opposed end of the spring is securely affixed to a base of the vaginal spring loaded delineator. Another objective is to prevent leakage of carbon dioxide from the peritoneal cavity when the vagina is opened laparoscopically. An enlarged portion, of the base of the vaginal spring loaded delineator, said enlarged portion is made to receive an elastic diaphragm made of an elastic material such as plastic: silicon, nylon, etc. The elastic diaphragm obstructs the vagina and prevents flow in any direction.

The extension of the base is made for insertion and locking into the head of the uterine mobilizer.

Another objective is to provide an elastic ring, made of plastic, which is put on the solid ring, and protects the ring as well as the instruments used to open the vagina laparoscopically, as may be the case with a harmonic scalpel, monopolar or bipolar electrosurgical instruments. Other objectives, advantages and novel features of the present invention will become apparent from the following detailed description of the invention when considered in conjunction with the accompanying drawings.

BRIEF DESCRIPTION OF THE SEVERAL VIEWS OF THE DRAWINGS

FIG. 2a is a plan view from the top of the first embodiment of the vaginal spring loaded delineator;

FIG. 2b is a side elevation view of the first embodiment of the vaginal spring loaded delineator;

FIG. 2c is a plan view from the bottom of the first embodiment of the vaginal spring loaded delineator;

FIG. 3a is a plan view from the top of an elastic diaphragm for the vaginal spring loaded delineator;

FIG. 3b is a cross section of the elastic diaphragm for the vaginal spring loaded delineator;

FIG. 5a is a plan view of the top of an elastic ring for the vaginal spring loaded delineator;

FIG. 5b is a cross section of the elastic ring for the vaginal spring loaded delineator;

FIG. 6 is a cutaway view of a female pelvis, the vaginal spring loaded delineator, being inserted and locked to a uterine mobilizer and inserted into the vagina;

DETAILED DESCRIPTION OF THE INVENTION

Figure 1:
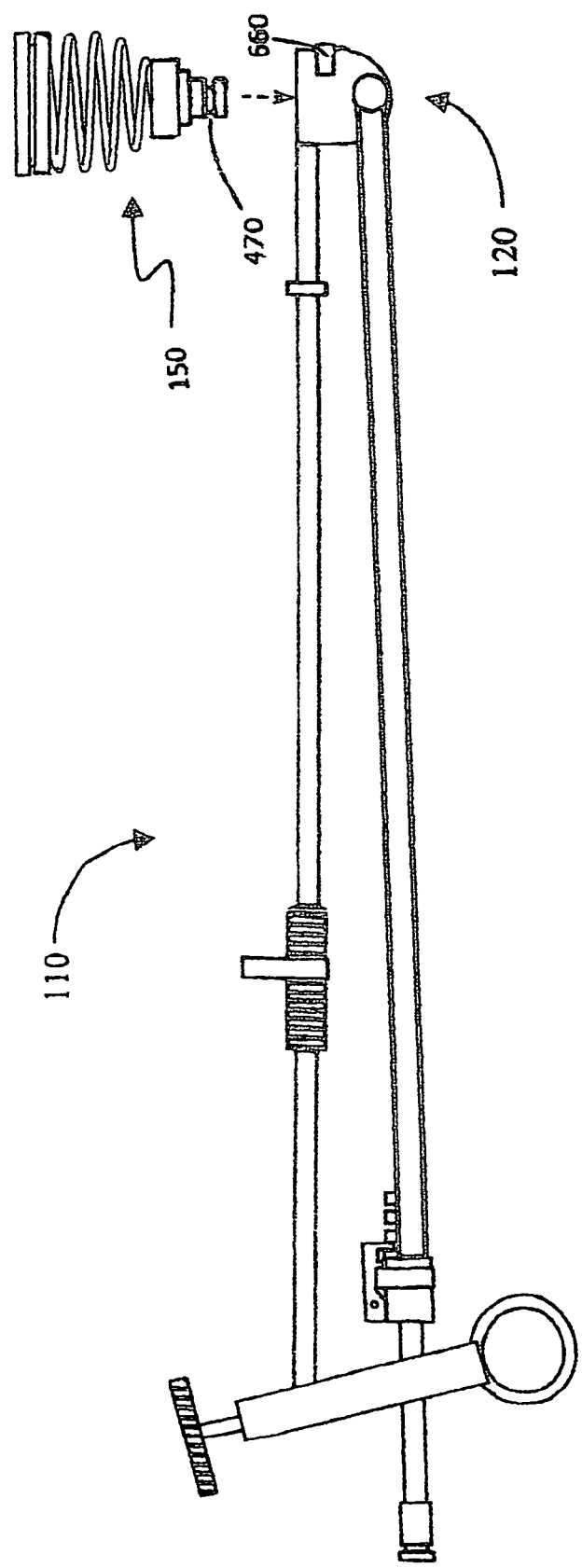
FIG. 1 is a side elevation view of a uterine mobilizer and a vaginal spring loaded delineator.
Figure 8A:
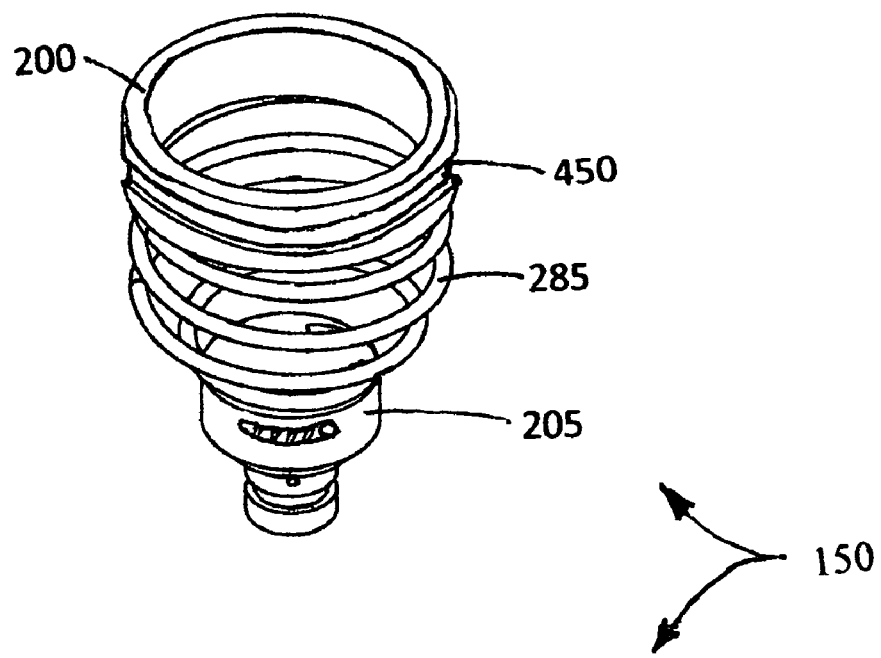
FIG. 8a is an oblique view from above of the second embodiment of the vaginal spring loaded delineator.
Figure 8B:
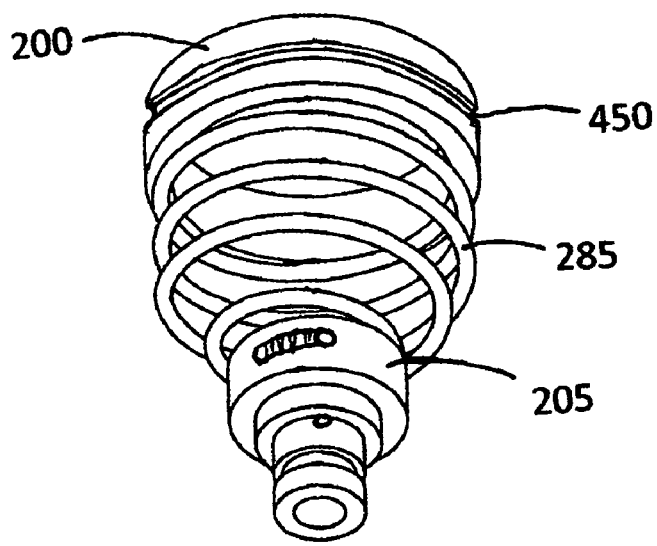
FIG. 8b is an oblique view from below of the second embodiment of the vaginal spring loaded delineator.

A first embodiment 150 of a vaginal spring loaded delineator is shown in FIG. 1, along with a uterine mobilizer 110 as disclosed in U.S. Pat. No. 5,562,679 which is hereby incorporated by reference. The first embodiment 150 is shown as well on FIGS. 8a-b. The second embodiment 160 of the vaginal spring loaded delineator is shown in details in FIGS. 2a-c. An enlarged portion 275 has an extension 250, which has a groove 470. The extension 250 is inserted and locked into the head 120 of the uterine mobilizer 110, FIG. 6. A groove 470, engages a lock 660 of the head 120 of the uterine mobilizer, see FIG. 1. On the proximal surface of the base 205, there is a hole 215 in which different length obturators can be inserted and locked in place by a lock 490, see FIGS. 2a-b. The proximal end of a spring 285 has a similar diameter to the diameter of the solid ring 200, and is securely affixed to the distal end of a solid ring 200.

The solid ring can have different diameters in order to fit the cervix 615, FIG. 6 which has different diameters.

Figure 4A:
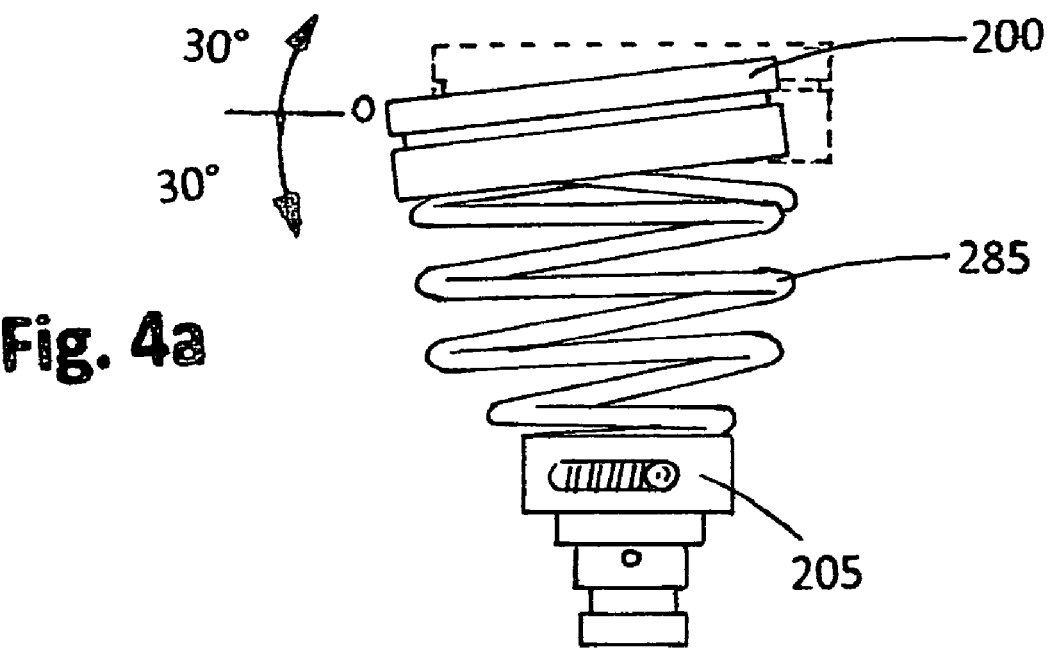
FIG. 4a is a side elevation view of the second embodiment of the vaginal spring loaded delineator showing the tilting of the solid ring.

The distal end of the spring has a similar diameter to the diameter of proximal end of the base 205 and is securely affixed to the proximal end of the base. The base has a smaller diameter than the diameter of the solid ring. The distal end of the spring has a few turns which have diminishing diameters until the last turn has a similar diameter to the diameter of the base. The solid ring 200 can tilt on the spring 285 in any direction, to about 30°, see FIG. 4a.

Figure 4B:
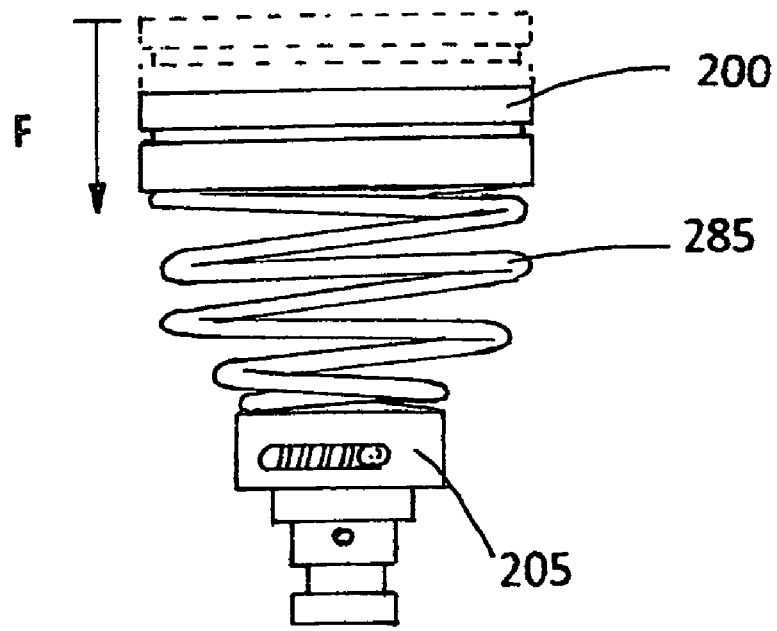
FIG. 4b is a side elevation view of the second embodiment of the vaginal spring loaded delineator, showing a change of the distance from the solid ring to the base.

When the solid ring is pushed F toward the fornix of the vagina, the spring is compressed, and the solid ring comes closer to the base. The length of the delineator can be reduced to about 50% of its length see FIG. 4b. The ability of the solid ring to be tilted in any direction permits automatic accommodation of the solid ring to the various angles of the vaginal fornix 620, FIG. 6. The ability of the solid ring, when pushed toward the fornix to come closer to the base, permits automatic accommodation of the cervices with different length.

When the vaginal spring loaded delineator 150 is attached to the uterine mobilizer 110 and is inserted into the vagina 610, FIG. 6, and is pushed toward the fornix 620, and when the solid ring 200 reaches the fornix 620, exerted pressure tilts the solid ring according to the spring is the fornix and comes closer to the base 205. The range of compression of the spring is determined by the length of the cervix. The coils of the spring surround the cervix 615. This relationship and function between the parts of the delineator—the solid ring, the spring and the base from one side and the cervix and the fornix of the vagina from the other side represent the novelty of this invention and are not found in the previous art.

Figure 7A:
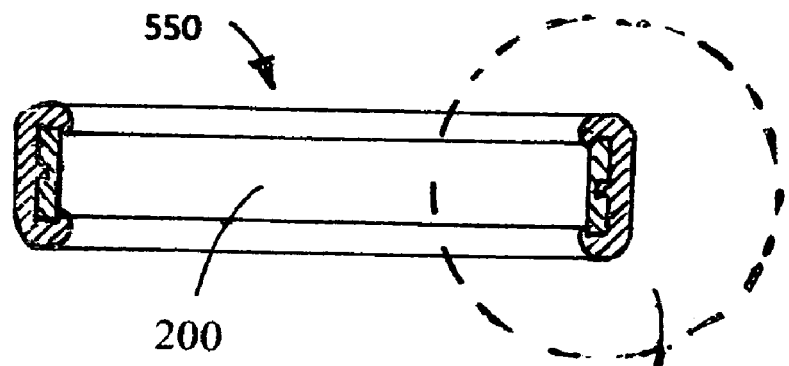
FIG. 7a is a cross section of the solid ring and the elastic ring put on the solid ring.
Figure 7B:
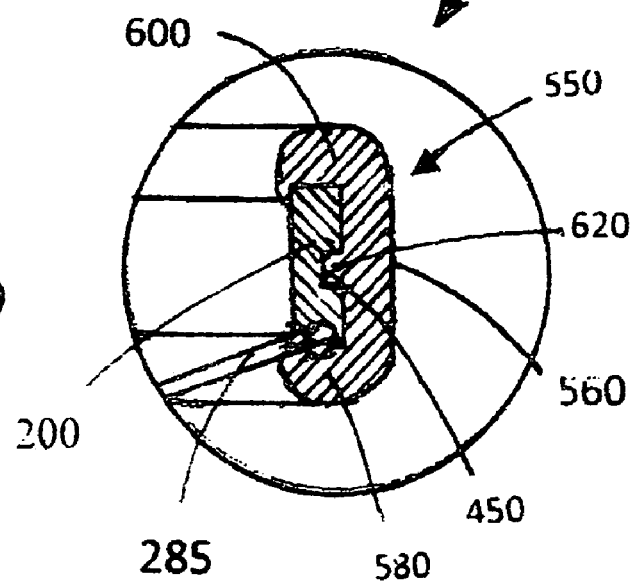
FIG. 7b is a partially enlarged cross section of the solid ring and the elastic ring put on the solid ring.

Over stretching of the spring 285, in the first embodiment 160 is prevented by securely affixing one end of a cable 290 (or chain, rope), to the solid ring 200 and the other end to the base 205, FIGS. 2a-c. The said cable 290 has the length of the spring 285. The only difference between the first embodiment 150 and the second embodiment 160 is the presence of cables in the second embodiment 160. The said cables prevent over stretching of the spring. An elastic ring 550, FIGS. 5a-b consists of a flat part 560 which distal end 580 and proximal end 600 are bended inward. There is an elevation 620 all around the inside surface of the elastic ring 550. The elastic ring is made from an elastic plastic like silicon, nylon, etc. The elastic ring 550 has a smaller diameter than the solid ring 200. The elastic ring has to be stretched before being put on the solid ring, this allows firm application of the elastic ring over the solid ring, see FIGS. 7a-b. The elevation 620 of the elastic ring engages the groove 450 of the solid ring 200, which makes it impossible for the elastic ring to come off during surgery, see FIG. 7b. The bended inward proximal 600 and distal 580 ends of the elastic ring, embrace the solid ring 200 and additionally keep the elastic ring firmly in place, preventing its dislodging during surgery, see FIG. 7b.

An elastic diaphragm 225 of elastic material such as plastic, nylon, silicon, etc., was described in the previous patent application Ser. No. 10/715,104, filed Nov. 17, 2003. It is shown in FIGS. 3a-b. and is presented here as a reference. Its use is to obstruct the vagina for the prevention of carbon dioxide leakage from the peritoneal cavity when the vagina is opened laparoscopically. The elastic diaphragm 225 has a hole 300 in its center through which an enlarged portion 275 Of the base 205 of the vaginal delineating and occluding device 100 passes. When the distal end of the base 205 is inserted in the uterine mobilizer 110, the diaphragm 225 is held securely between the base 205 and the head of the mobilizer 110. Various sizes of diaphragms 225 may be supplied to fit a variety of patients. The rim 310 and the annulus 320 are thicker than a membrane 330, FIGS. 3a-b.

The above embodiments are the preferred embodiments, but this invention is not limited thereto. It is, therefore, apparent that many modifications and variations of the present invention are possible in light of the above teachings. It is, therefore, to be understood that within the scope of the appended claims, the invention may be practiced otherwise than as specifically described.

I claim:

1. A method of constructing a vaginal spring loaded delineator comprising a solid ring, a spring, including a proximal end having a larger diameter and a distal end having a smaller diameter, a base, an enlarged portion and an extension of a base for inserting and locking said apparatus to a uterine mobilize; said method comprising;
    (a) securely affixing the proximal end of a spring to the distal end of a solid ring; and
    (b) securely affixing the distal end of the spring to the proximal end of the base;
    (c) wherein applying force to the solid ring by pushing the vaginal spring-loaded delineator toward the fornix of a vagina of a user allows the solid ring to tilt in any direction, to come closer to the base and to self-adjust to the angle of the fornix and a length of the cervix.

2. A method of claim 1 wherein the proximal end of the spring has a similar diameter to the diameter of the solid ring and the distal end has a similar diameter to the diameter of the base.

3. A method of claim 1 wherein a last few turns of the spring have diminishing diameters until a last turn has a similar diameter to the diameter of the base.

4. A method of claim 1 wherein by the extension of the base of the vaginal spring loaded delineator can be inserted and locked to a uterine mobilize.

* * * * *